United States Patent
Peatfield et al.

(10) Patent No.: US 10,201,315 B2
(45) Date of Patent: Feb. 12, 2019

(54) FLUID ANALYZER AND ASSOCIATED METHODS

(71) Applicant: Atrium Medical Corporation, Hudson, NH (US)

(72) Inventors: Greg Peatfield, Atkinson, NH (US); Ted Karwoski, Hollis, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 573 days.

(21) Appl. No.: 14/212,336

(22) Filed: Mar. 14, 2014

(65) Prior Publication Data
US 2014/0323906 A1   Oct. 30, 2014

Related U.S. Application Data

(60) Provisional application No. 61/794,712, filed on Mar. 15, 2013.

(51) Int. Cl.
*A61B 5/00* (2006.01)
*A61M 1/00* (2006.01)
(Continued)

(52) U.S. Cl.
CPC .......... *A61B 5/7267* (2013.01); *A61B 5/036* (2013.01); *A61B 5/742* (2013.01); *A61B 5/7475* (2013.01);
(Continued)

(58) Field of Classification Search
CPC .. A61B 5/021; A61B 5/03; G01L 7/00; G01L 27/00
See application file for complete search history.

(56) References Cited

U.S. PATENT DOCUMENTS 4,654,029 A * 3/1987 D'Antonio .......... A61M 1/0031
600/584
5,195,995 A * 3/1993 Walker ................ A61M 1/0013
604/319
(Continued)

FOREIGN PATENT DOCUMENTS

CN 1266179 A 9/2000
CN 101277734 A 10/2008
(Continued)

OTHER PUBLICATIONS http://www.encyclopedia.com/doc/1G2-3045000716.html Linear Hypotheses International Encyclopedia of the Social Sciences | 1968 | 700+ words Copyright 2008 Thomson Gale.*
(Continued)

*Primary Examiner* — Sean Dougherty
*Assistant Examiner* — Patrick Fernandes
(74) *Attorney, Agent, or Firm* — Wesley Scott Ashton; Kevin T. Godlewski

(57) ABSTRACT

Devices, computer readable programs and methods determine a patient parameter, including volume and/or flow rate of a fluid draining through a drain tube from a chest cavity of a patient, by using at least one pressure value at an end of the drain tube associated with a fluid collection canister and at least one pressure value within the drain tube at a location distant from the collection canister. The pressure values are processed with a non-linear solver to determine the patient parameter.

10 Claims, 6 Drawing Sheets

(51) Int. Cl.
*A61B 5/03* (2006.01)
*A61B 5/08* (2006.01)

(52) U.S. Cl.
CPC .......... *A61M 1/008* (2013.01); *A61M 1/0019* (2013.01); *A61M 1/0031* (2013.01); *A61B 5/0816* (2013.01); *A61B 5/4848* (2013.01); *A61B 5/6852* (2013.01); *A61B 5/7225* (2013.01); *A61M 2205/3334* (2013.01); *A61M 2205/3344* (2013.01); *A61M 2205/3389* (2013.01); *A61M 2205/52* (2013.01); *A61M 2210/101* (2013.01)

(56) References Cited

U.S. PATENT DOCUMENTS

| | | | |
|---|---|---|---|
| 2004/0058432 | A1 | 3/2004 | Owen et al. |
| 2005/0154359 | A1 | 7/2005 | Charlez |
| 2007/0019865 | A1 | 1/2007 | Owechko et al. |
| 2010/0280334 | A1 | 11/2010 | Carlson et al. |
| 2011/0022335 | A1* | 1/2011 | Foucault ............... G01F 1/36 702/47 |
| 2011/0071415 | A1* | 3/2011 | Karwoski ............... A61B 5/08 600/529 |
| 2012/0059340 | A1 | 3/2012 | Larsson |
| 2012/0303564 | A1* | 11/2012 | Dobson ............... G06F 19/345 706/21 |
| 2014/0019094 | A1* | 1/2014 | Parvin ............... G01T 1/169 702/189 |

FOREIGN PATENT DOCUMENTS

| | | |
|---|---|---|
| JP | 5993372 | 8/2016 |
| WO | 2013/003970 A1 | 1/2013 |

OTHER PUBLICATIONS

International Search Report and Written Opinion dated Aug. 18, 2014 for corresponding International Application No. PCT/US2014/029319, 17 pages.

Extended European Search Report dated Oct. 7, 2016 for corresponding European Patent Application No. 14762310.2, 7 pages.

Chinese Office Action and Chinese Search Report (both in English and Chinese) dated Dec. 20, 2016 for corresponding Chinese Patent Application No. 201480024298.8, 19 pages.

Louis Esch et al., "Appendix 8—Numerical Methods for Solving Nonlinear Equations"—Asset and Risk Management: Risk Oriented Finance (John Wiley & Sons Ltd. 2005)—pp. 375-381.

Office Action issued for counterpart JP Application No. 2016-503058, dated Jan. 30, 2018.

Examination Report issued in counterpart AU Application No. 2014228778, dated Jul. 9, 2018, 5 pages.

* cited by examiner

FLUID ANALYZER AND ASSOCIATED METHODS

RELATED APPLICATIONS

This application claims priority to a provisional application Ser. No. 61/794,712 filed Mar. 15, 2013, the entire content of which is hereby incorporated by reference.

STATEMENT REGARDING FEDERAL SPONSORSHIP

Embodiments of the present invention were not conceived or reduced to practice with Federal sponsorship or grants.

FIELD OF THE INVENTION

Embodiments of the present invention are directed to equipment and methods of treatment in which it is desired to know the amount of fluid removed from a source of fluid such as the chest cavity of an individual.

BACKGROUND

There are several disease states and injuries for which it is desirable to remove fluids from the chest cavity of the afflicted individual. Clinicians monitor the amount of fluid removed in order to determine the progression of the healing process, the progression of the disease and the function of the devices used to effect such drainage. Typically, the patient has a drainage tube inserted into the chest cavity and the tube drains into a special closed container known as a chest drain unit (CDU). There are various means to measure the fluid in the sealed container and each is associated with a cost, either in clinician time in making an observation or measurement, or in equipment cost in providing sensors and signaling devices for making a measurement and bringing the measurement data to the attention of the clinician or a hospital information system.

For example, without limitation, some devices feature one or more strain gauges for measuring the weight or changing weight of a container. As the accuracy of the strain gauge increases, the gauge becomes more expensive and more susceptible to damage. Strain gauges in particular are easily damaged, and if designed to be more robust have less resolution to weight change.

Clinical staff monitoring of a patient on a CDU, required to record fluid drainage volume levels of a patient, is awkward, time consuming and, therefore, costly and not measured or checked as often as otherwise might be desirable. The drainage devices are usually kept on the floor and require a clinician to get down on hands and knees to read the fluid levels, and remember to adjust for errors should for instance the CDU accidentally be knocked over during use.

SUMMARY OF THE INVENTION

Embodiments of the present invention are directed methods, computer programs and devices for determining at least one patient parameter, in a patient having the drain tube having a first end and a second end, the first end fitted into the patient chest cavity and a second end received in a collection vessel. As used herein, the term "patient parameter" refers to a patient parameter associated with the drain tube, including, by way of example, without limitation, volume of fluid (gas and/or liquid) removed from the chest cavity, the flow rate of the fluid being removed, the present volume of the container holding the liquid portion of the removed fluid, present function of filtering devices and tubes, and patient breathing status.

Embodiments of the present method, computer program and device feature at least one of the collection vessel and a drain tube having a first pressure sensor sensing the pressure within at least one of (i) the drain tube in a location proximal to the collection vessel and (ii) the collection vessel, and a second pressure sensor sensing the pressure within the drain tube at a location distal to the collection vessel. That is, the first pressure sensor is closely associated with the collection vessel either located within the collection vessel or in the drainage tube close to the collection vessel. The second pressure sensor is positioned in the drainage tube away from the collection vessel, more proximal to the patient.

The method comprises the steps of obtaining at least a first pressure value from the first pressure sensor and at least a first pressure value from the second pressure sensor. The method further comprises the step calculating at least one patient parameter by the pressure values through a non-linear solver.

One embodiment of the present method features associating each pressure value with a time and obtaining a plurality of successive pressure values over time. The successive pressure values are preferably separated in time at timed intervals; that is, it is periodic.

Embodiments of the present method are well suited for performance by computer means. As used herein, the term "computer means" refers to computer or central processing units (CPUs), internal to a device or carried separate and distinct from a device, such as CPUs carried on mainframe computers, servers, conventional desktop and laptop computers, microcontrollers, board computers such as Raspberry Pi, and handheld communication devices such as cell phones and tablet devices, off-site computers linked through internet and/or wireless communication devices and the like. Preferably, the first pressure values and successive pressure values are stored in computer memory. As used herein, the term "computer memory" refers to data storage such as chips, disks, memory drives, hard drives, flash drives and the like that are in signal communication with the CPU and can be processed by such CPU. For example, the CPU accesses such first in time pressure values and the successive pressure values from memory and performs the step of organizing such data, calculating at least one patient parameter and produces an output displaying the one patient parameter.

As used herein, the term "non-linear solver" refers to a machine learning process in a hypothesis/model mathematical computer program sense. The non-linear solver is trained with known inputs and outputs and the trained non-linear solver is exported or programmed to receive the first pressure value and second pressure value and all other successive pressure values, process such values through the hypothesis/model to obtain a patient parameter.

Embodiments feature a non-linear solver implemented in one or more approaches selected from the group consisting of Support Vector Machine Approach, Artificial Neural Networks, Genetic Algorithms and Genetic Programming. The detailed discussion will describe a non-linear equation in the form of a linear regression hypothesis and machine learning processes.

For example, one non-linear equation is the linear regression hypothesis:

$$h(T) = f(P_c(t), P_v(t)) = Theta_{bias} + \sum_{j=0}^{N} [Theta_{c,j} * P_C(j) + Theta_{V,j} * P_V(j)]$$

As used above:
T=Represent current time (t=0), or point at fixed time after data
t=Integer time sample, 0 most current, N—oldest
f(x,y)=An unknown function dependent upon x & y
h(T)=Volume of fluid in fluid canister
$P_V(t)$=Pressure as a function of time at Vent,
$P_C(t)$=Pressure at CDU side of patient as a function of time,
N=Number of time samples required for calculation
Theta=Set of all Theta's listed below
$Theta_{bias}$=Arbitrary DC bias constant for hypothesis
$Theta_{c,t}$=Arbitrary parameter coefficient for CDU Pressure at time t
$Theta_{V,t}$=Arbitrary parameter coefficient for Vent Pressure at time t.

The linear regression equation has a cost function J expressed with training set of "m" values, expressed as follows:

$$J(Theta) = \frac{1}{2*m} \sum_{i=1}^{m} [h(T)^i - V(T)^i]^2$$

The unknown "Theta" values are determined with training set of 'm' items as follows:

$$\min_{Theta} J(Theta) = \frac{1}{2*m} \sum_{i=1}^{m} [h(T)^i - V(T)^i]^2$$

For example, without limitation, the non-linear equation and its derivatives are solved by one or more optimization algorithms chosen from the group consisting of Gradient Descent, Particle Swarm Optimization and Artificial Bee Colony.

The one method features Theta derived as follows:

$$Theta_x = Theta_x - \alpha * \frac{\partial}{\partial Theta_x} J(Theta)$$

with the partial derivative for J(Theta) with $X_x$ being the Bias, Pv or Pc parameter associated with $Theta_x$ expressed as:

$$\frac{\partial}{\partial Theta_x} J(Theta) = \frac{1}{m} \sum_{i=1}^{m} [h_{Theta}(T)^i - V_{Theta}(T)^i] * X_x^i.$$

A further non-linear equation embodying features of the present invention is expressed as:

$$h(T) =$$
$$f(P_c(t), P_v(t)) = Theta_{bias} + \sum_{j=0}^{N} [Theta_{C1,j} * P_C(j) + Theta_{C2,j} * P_C(j)^2 +$$
$$Theta_{V1,j} * P_V(j) + Theta_{V2,j} * P_V(j)^2]$$

wherein:
T=Represent current time (t=0), or point at fixed time after data
t=Integer time sample, 0 most current, N—oldest
f(x,y)=An unknown function dependent upon x & y
h(T)=Volume of fluid in fluid canister
$P_V(t)$=Pressure as a function of time at Vent,
$P_C(t)$=Pressure at CDU side of patient as a function of time,
N=Number of time samples required for calculation
Theta=Set of all Theta's listed below
$Theta_{bias}$=Arbitrary DC bias constant for hypothesis
$Theta_{c,t}$=Arbitrary parameter coefficient for CDU Pressure at time t
$Theta_{V,t}$=Arbitrary parameter coefficient for Vent Pressure at time t.

A further embodiment of the present invention is directed to computer readable program for determining at least one patient parameter. The computer readable program comprises instructions for a computer processing unit having memory to obtain at least one first pressure value from the first pressure sensor and at least one first pressure value from the second pressure sensor. The computer readable program further instructs computer means to calculate at least one patient parameter by the pressure values through a non-linear solver.

The computer readable program operates or runs on computer means, to receive the at least one first pressure values and any successive pressure values over time, for example, at timed intervals, and store such data in memory. The data is organized and used to calculate one or more patient parameters for display. It is processed in accordance with the non-linear equations and methods described above.

A further embodiment of the present invention is directed to a device for determining at least one patient parameter. The device comprises a first pressure sensor constructed and arranged to sense the pressure within at least one of (i) the drain tube in a location proximal to the collection vessel or (ii) the collection vessel itself, and a second pressure sensor constructed and arranged to sense the pressure within the drain tube at a location distal to the collection vessel. The first pressure sensor and the second pressure sensor are constructed and arranged for being placed in signal communication with computing means having memory for obtaining a first pressure value from the first pressure sensor and a first pressure value from the second pressure sensor. The computer means calculates at least one patient parameter by the pressure values through a non-linear solver.

A preferred device comprises a computer means. The computer means preferably receives a plurality of first pressure values and any successive pressure values over time, for example, without limitation, at timed intervals, which are stored in memory, organized and processed to calculate one patient parameter.

The data is organized and used to calculate one or more patient parameters for display. It is processed in accordance with the non-linear equations and methods described above and described more fully in the detailed description that follows.

The methods, computer readable programs and devices of the present invention allow monitoring of fluids removed from the chest cavity of a patient. Such fluids comprise any biological fluid such as gas, water, serum, blood, plasma, lymph, pus therapeutic infusion fluids and mixtures thereof. The term "gas" is used to refer to air and gases administered for therapeutic purposes, such as, oxygen, nitrogen, helium and nitric oxide. Embodiments of the present method computer readable program and device allow the calculation of the gas volume and the liquid volume and corresponding flow rate of the fluid.

These and other features and advantages will be apparent to those skilled in the art upon viewing the Figures described briefly below and studying the detailed description of the invention that follows.

DETAILED DESCRIPTION OF THE EMBODIMENTS

Figure 1:
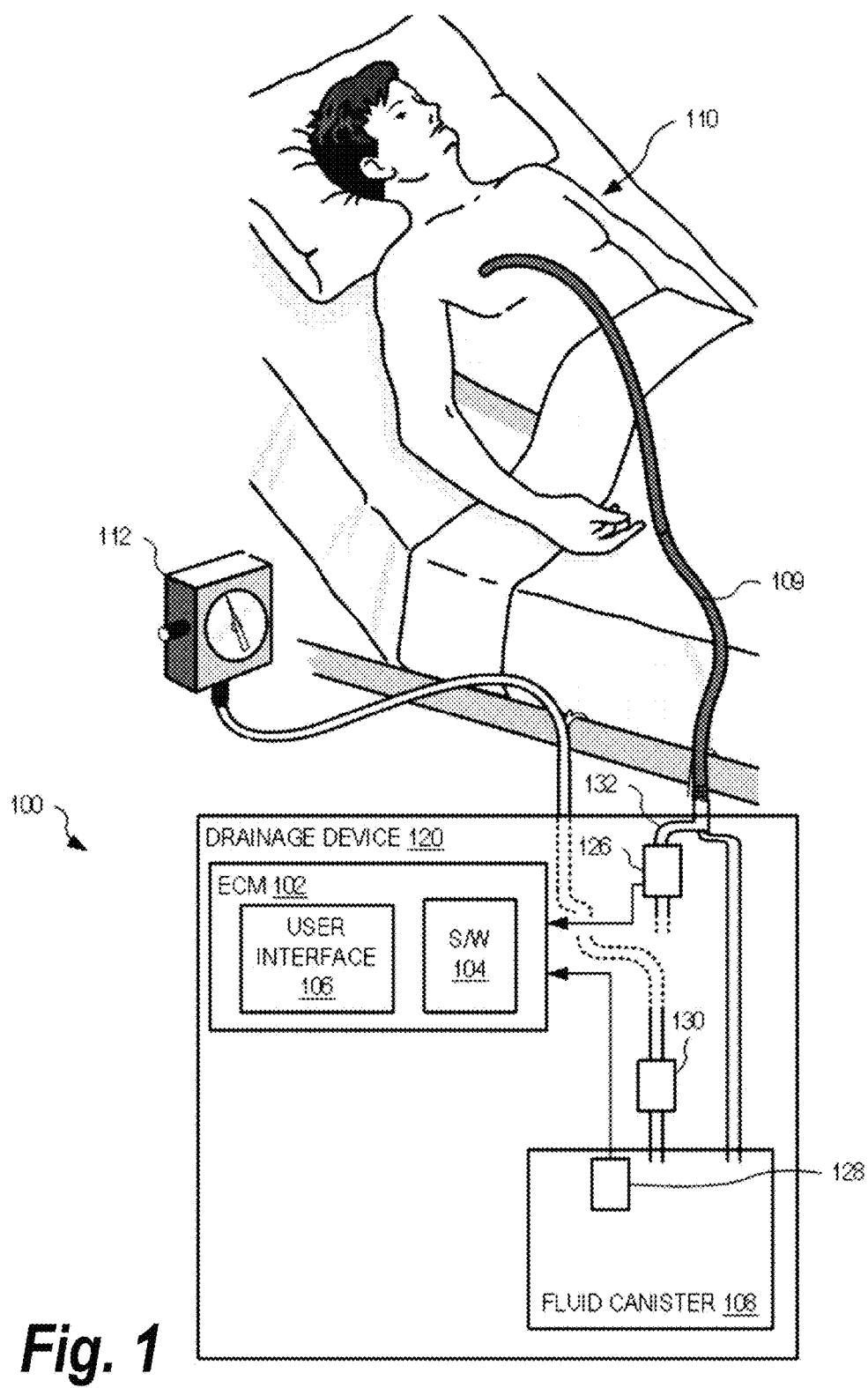
FIG. 1 shows one exemplary fluid analyzer for determining volume and/or flow of fluid draining from a chest cavity of a patient, according to an example embodiment.

Embodiments of the present invention will be described in detail with respect to a device, system and method for measuring fluid volumes from an external source such as a chest cavity of a patient. Turning now to FIG. 1 a device embodying features of the present invention, sometimes referred herein as fluid analyzer, and generally designated by the numeral 100, is depicted.

FIG. 1 shows one exemplary fluid analyzer 100 for determining volume and/or flow of fluid draining from source such as a chest cavity of a patient 110. In the example of FIG. 1, fluid analyzer 100 is implemented within a drainage device 120 that operates, for example, to collect fluid drained from a chest cavity of a patient 110 using a catheter or tubing such as a double-lumen catheter 109. In the example of FIG. 1, drainage device 120 is shown coupled to a vacuum source 112 to facilitate fluid drainage from patient 110.

Drainage device 120 is shown to include an electronic control module (ECM) 102 that operates to control drainage of fluid through catheter 109 into a fluid canister 108. As depicted, ECM 102 includes a user interface 106 for interacting with a user (e.g., clinical staff) of device 120. Fluid canister 108 is for example a chest drainage unit (CDU) that collects fluid draining from a chest cavity of a patient. ECM 102 receives pressure values from (a) a vent pressure sensor 126 that senses pressure near the patient connection of a vent pathway of catheter 109 and (b) a CDU pressure sensor 128 that senses pressure at the end of a drain tube and collection system that originates from the same patient point. Vent pressure sensor 126 may be located on the drain pipe of catheter 109, particularly where catheter 109 is not of a double lumen type. Additional pressure sensors, positioned with drainage device 120 and/or catheter 109, may be used with system 100 without departing from the scope hereof.

Drainage device 120 may include other components (e.g., valves, filters, sensors, converts, interfaces, etc.) without departing from the scope hereof. Drainage device 120 processes a time series of pressure values from pressure sensors 126 and 128 to determine fluid volume and/or flow rate of fluid drained from patient 110. ECM 102 may determine other metrics such as, but not limited to: CDU filter clogging, patient breathing, patient inhaling, patient exhaling, breaths/min, patient in respiratory distress (e.g., coughing, choking, laughing, crying, etc.), tube clogs and the degree of occlusion or clogging, fluid in line, and patient dumping of fluid.

Figure 2:
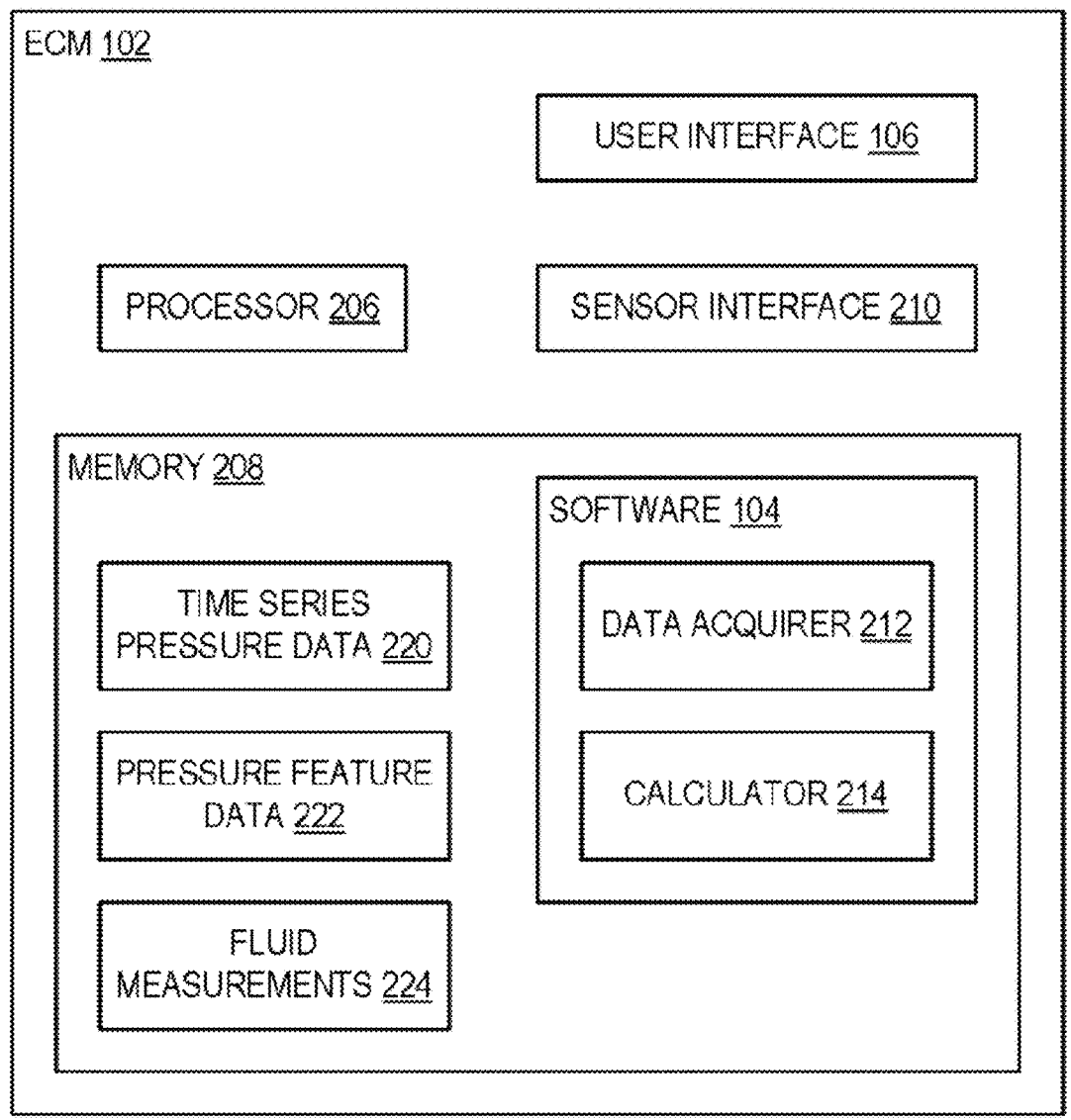
FIG. 2 is a schematic showing the electronic control module of FIG. 1 in further exemplary detail, according to an example embodiment.

FIG. 2 is a schematic showing ECM 102 in further exemplary detail. FIGS. 1 and 2 are best viewed together with the following description. ECM 102 is shown to include a user interface 106, a processor 206, a memory 208, and a sensor interface 210. Memory 208 is illustratively shown storing software 104 that includes machine readable instructions that when executed by processor 206 implements functionality within drainage device 120 for determining a volume and/or flow rate of the fluid draining from patient 110. Sensor interface 210 couples with both vent pressure sensor 126 and CDU pressure sensor 128 and includes an analog to digital converter to provide sensed pressure values to software 104. Software 104 includes a data acquirer 212 and a calculator 214. Data acquirer 212 operates to collect pressure values from pressure sensors 126 and 128 over time and stores these values as time series pressure data 220 within memory 208. Time series pressure data 220 contains pressure values read periodically from pressure sensors 126 and 128 via sensor interface 210. Calculator 214 operates to process time series pressure data 220 to determine volume of fluid within canister 108 and optionally determines a flow rate of fluid into canister 108. Calculator 214 may include a learning algorithm that automatically learns, based upon pressure values read from sensor interface 210 and defined volumes, a relationship between these pressure values and fluid volume and/or flow rate. Calculator 214 generates pressure feature data 222 based upon identified pressure variations at each pressure sensor 126 and 128. Pressure feature data 222 may be referred to hereinafter as vent pressure features and/or CDU pressure features. Calculator 214 also generates fluid measurements 224 to include one or both of fluid volume within canister 108 and fluid flow rate into canister 108. Data acquirer 212 and calculator 214 may operate concurrently.

Figure 3:
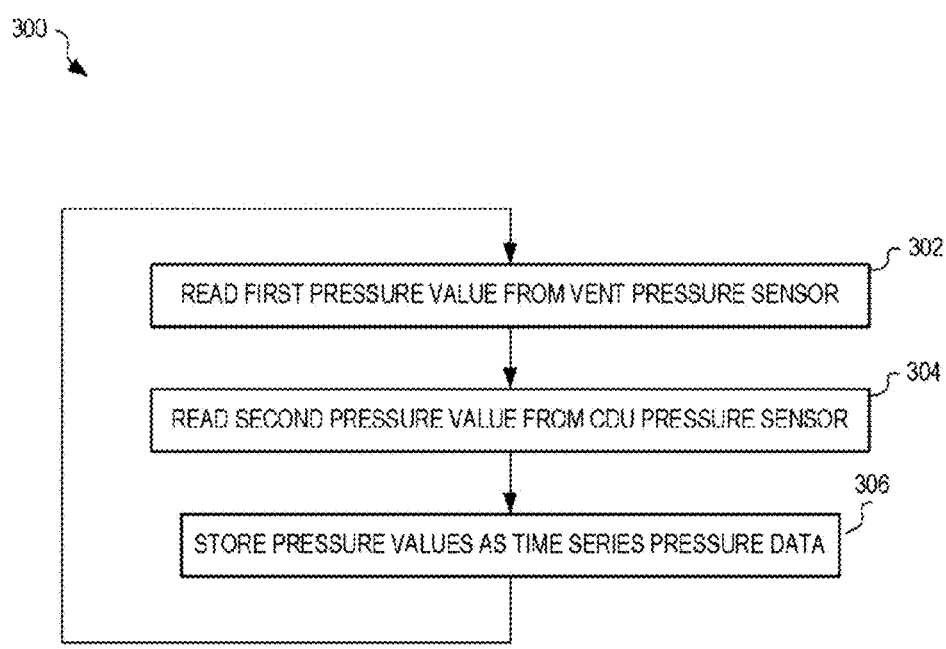
FIG. 3 is a flowchart illustrating one exemplary method for collecting and storing time series pressure values, according to an example embodiment.
Figure 4:
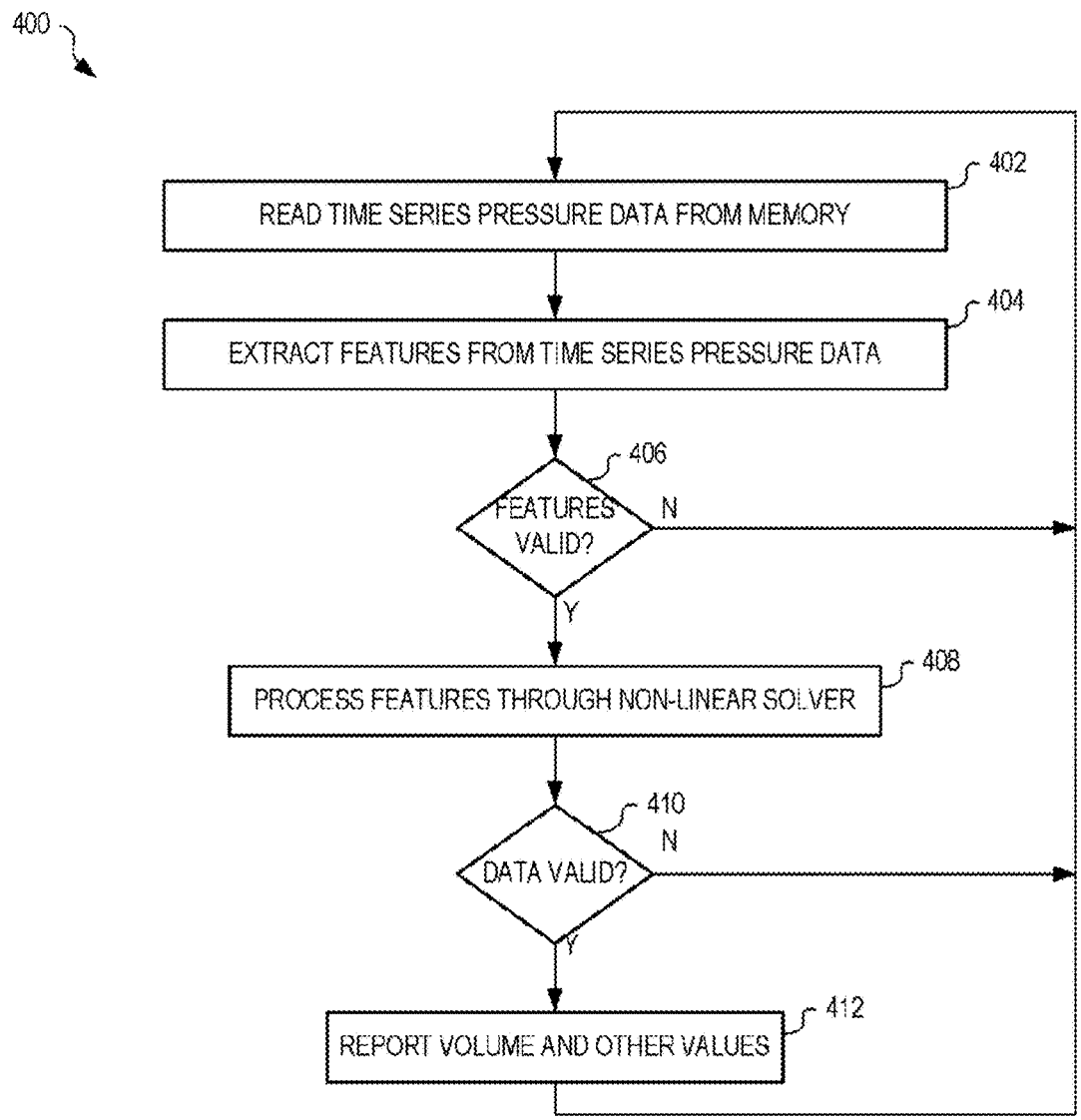
FIG. 4 is a flowchart illustrating one exemplary method for processing the stored time series pressure values of FIG. 3 for measurement of chest drain fluid, according to an example embodiment.

FIG. 3 is a flowchart illustrating one exemplary method 300 for reading and storing time series pressure values. FIG. 4 is a flowchart illustrating one exemplary method for processing the stored time series pressure data for measurement of chest drain fluid. Methods 300 and 400 are for example separate processing threads running on a computer is implemented within software 104 of ECM 102, for example. FIGS. 1 through 4 are best viewed together with the following description.

In step 302, method 300 reads a first pressure value from the vent pressure sensor. In one example of step 302, software 104, executed by processor 206, reads the first pressure value from vent pressure sensor 126 using sensor interface 210. In step 304, method 300 reads a second pressure value from the CDU pressure sensor. In one example of step 304, software 104, executed by processor 206, reads the second pressure value from CDU pressure sensor 128 using sensor interface 210.

In step 306, method 300 stores the pressure values of steps 302 and 304 as time series pressure data. In one example of step 306, data acquirer 212 stores pressure values of steps 302 and 304 within memory 208 as time series pressure data 220.

Method 300 repeats periodically to collect and store pressure values and calculates fluid parameters based upon the first and second pressure values.

In step 402, method 400 reads time series pressure data from memory. In one example of step 402, calculator 214 reads time series pressure data 220 from memory 208. In step 404, method 400 extracts features from the time series pressure data. In one example of step 404, calculator 214 extracts pressure features from time series pressure data 220 and stores these pressure features as pressure feature data 222 within memory 208.

Step 406 is a decision. In step 406, method 400 determines whether the features determined in step 404 are valid, and if these features are valid, method 400 continues with step 408; otherwise method 400 continues with step 402.

In step 408, method 400 processes the features through a non-linear solver. In one example of step 408, calculator 214 processes pressure feature data 222 through a non-linear equation to generate fluid measurements 224 that include one or both of fluid volume and fluid flow rate. In another example of step 408, calculator 214 processes pressure feature data 222 through a pre-trained Support Vector Machine. In another example of step 408, calculator 214 processes pressure feature data 222 using one or more of Artificial Neural Networks, Genetic Algorithms, and Genetic Programming. For example, calculator 214 may utilize data based upon one or more of collected training, validation and testing data sets.

Step 410 is a decision. In step 410, method 400 determines whether the data generated in step 408 is valid, and if this data is valid, method 400 continues with step 412; otherwise method 400 continues with step 402.

In step 412, method 400 reports the determined volume and other values. In one example of step 412, calculator 214 outputs fluid measurements 224 to user interface 106.

Method 400 repeats periodically to determine and output fluid measurements 224 based upon time series pressure data 220.

Figure 5:
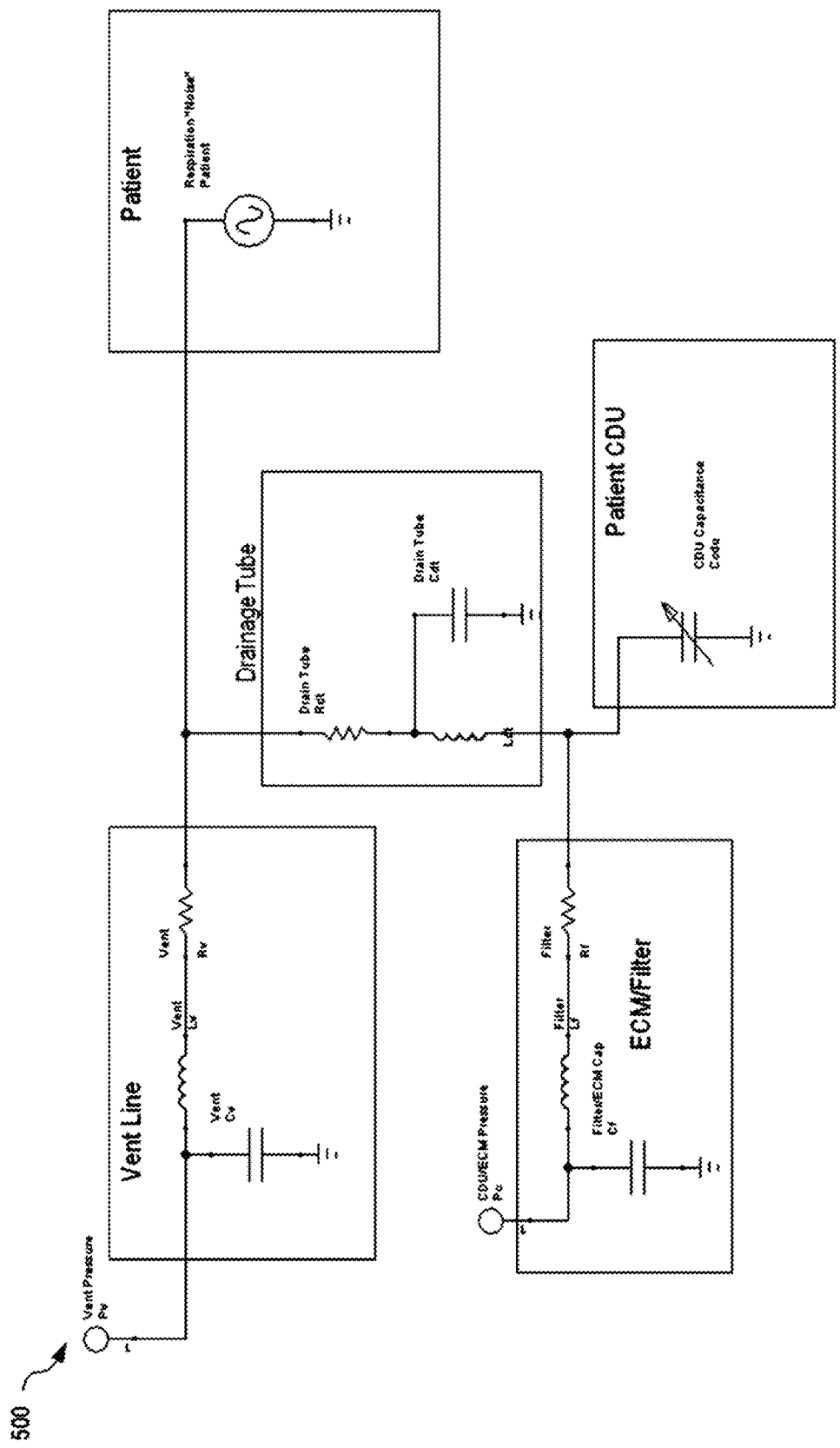
FIG. 5 is a schematic illustrating one exemplary electronic circuit that models the drainage device of FIG. 1, according to an example embodiment.

FIG. 5 shows one electronic analog 500 representing the resistance, inductance, and capacitance of different sections of drainage device 120. Thus, according to an example embodiment, electronic analog 500 models drainage device 120. Drainage device 120, however, could alternately be modeled in other manners without departing from the scope hereof. Electronic analog 500 is fixed for both branches, with the single exception of fluid canister 108, which is modeled by a variable capacitor. Given the dynamic pressure signal created by the patient and the "electrical network" differences "seen" by each pressure sensor 126, 128, this timing will vary non-linearly depending upon the fluid volume within fluid canister 108. An increase in fluid volume in fluid canister 108 will decrease the air capacity in the leg of the circuit affecting the pressure timing. The Filter (Rf of FIG. 5) could vary in resistance (increase over time) within the system. This resistance variation should be a linear affect and occur gradually over time.

Figure 6:
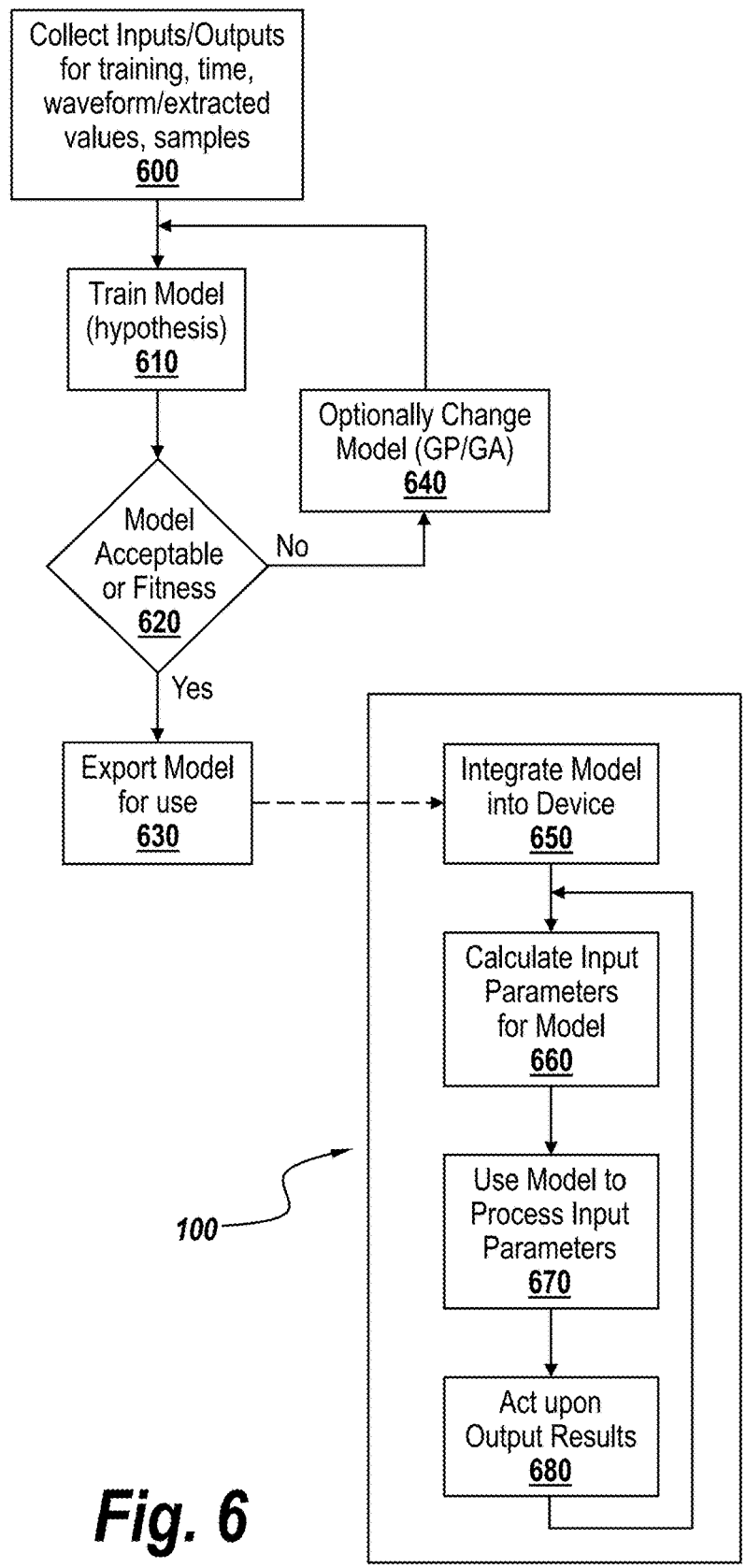
FIG. 6 depicts a machine learning process, according to an example embodiment.

FIG. 6 depicts a machine learning process for a system or device 100. Steps 600, 610, 620 and 640 are characterized as training. The step 600 is collecting inputs and outputs for training. These inputs and outputs would be obtained experimentally in a controlled setting to produce a matrix of inputs and outputs in the training step 610. The training step 610 produces one or more outputs which are evaluated for acceptance or fitness. Genetic Algorithms and Programs evaluates inputs and outputs on the basis of fitness based upon desired outputs and upon all expected outputs during training compiled in to one value with optional changes to the model at step 640. If the model produces acceptable results, the model is exported at step 630 to device 100.

The model is integrated into the device 100 at step 650. And, the model is used to calculate input parameters for the model at step 660. The model is used to process the input parameters at step 670 and at step 680, the device 100 acts upon the output results.

Exemplary Approach:

In certain embodiments, a non-linear equation hypothesis is used to calculate the volume of fluid in fluid canister 108. Either a fixed model or dynamic and self-correcting model may be used. A fixed model is typically desired so that constants (weights or masses) do not change and can be used as-is within the software 104 without retraining. The hypothesis would be the same for either the fixed model or the dynamic and self-correcting model, but the equation may need to be optimized for the model.

Hypothesis:

LET:

T=Represent current time (t=0), or point at fixed time after data t=Integer time sample, 0 most current, N—oldest f(x,y)=An unknown function dependent upon x & y J(Theta)=Cost of hypothesis vs actual for Theta V(T)=Volume of fluid in fluid canister 108 (actual)

h(T)=Volume of fluid in fluid canister 108 (hypothesis)

$P_V(t)$=Pressure as a function of time at Vent, determined from pressure sensor 126, for example (Or vent pressure features, and other parameters)

$P_C(t)$=Pressure at CDU side of patient as a function of time, determined from pressure sensor 128, for example (Or CDU pressure features, and other parameters)

m=Number of samples in training set

N=Number of time samples required for calculation

Theta=Set of all Theta's listed below $Theta_{bias}$=Arbitrary DC bias constant for hypothesis $Theta_{c,t}$=Arbitrary parameter coefficient for CDU Pressure at time t $Theta_{V,t}$=Arbitrary parameter coefficient for Vent Pressure at time t To approximate V(T), set the following Linear Regression hypothesis:

$$h(T) = f(P_c(t), P_v(t)) = Theta_{bias} + \sum_{j=0}^{N}[Theta_{c,j} * P_C(j) + Theta_{V,j} * P_V(j)]$$

A cost function J can be expressed as shown with training set of 'm' items as follows:

$$J(Theta) = \frac{1}{2*m}\sum_{i=1}^{m}[h(T)^i - V(T)^i]^2$$

Unknown "Theta" values can be found with training set of 'm' items as follows:

$$\min_{Theta} J(Theta) = \frac{1}{2*m} \sum_{i=1}^{m} [h(T)^i - V(T)^i]^2$$

There are a number of ways this equation may be solved or modified. One possible approach to solving or modifying the equation is through the use of a "Gradient Descent" approach/algorithm. Gradient Descent approaches provide a good approximation of solutions for the equation. Alternative methods include more recent and faster optimization systems, such as Particle Swarm Optimization systems. The equation is capable of being solved rapidly with low overhead using Artificial Bee Colony (ABC). Another approach is to use an external math package such as MatLab, R, or Octave, to solve for "Theta". These solution approaches are known in the art. These values of Theta are, for example, entered or otherwise incorporated into ECM 102, such as in the form of software 104. This approach is typically sufficient for any static "Theta" group.

Gradient Descent requires the partial derivative for the cost function in terms of "Theta" to move "Theta" downhill as follows:

$$Theta_x = Theta_x - \alpha * \frac{\partial}{\partial Theta_x} J(Theta)$$

The partial derivatives for J(Theta) with $X_x$ being the Bias, Pv or Pc parameter associated with $Theta_x$ can be expressed as:

$$\frac{\partial}{\partial Theta_x} J(Theta) = \frac{1}{m} \sum_{i=1}^{m} [h_{Theta}(T)^i - V_{Theta}(T)^i] * X_x^i$$

If the above equation hypothesis does not converge, second power terms, and potentially even third power terms, may be added to help achieve convergence. Such incorporation of additional power terms will be required if the solution exhibits a high bias condition (under-fit). The opposite problem may occur if too many parameters are present, which is referred to high variance (over-fit). Overfitting can be resolved through a number of techniques, such as regularization and adding more samples.

The following is second equation hypothesis including higher degree terms, which is used, for example, if first order model does not satisfactorily converge:

$$h(T) = f(P_c(t), P_v(t)) = Theta_{bias} + \sum_{j=0}^{N} [Theta_{C1,j} * P_C(j) + Theta_{C2,j} * P_C(j)^2 + Theta_{V1,j} * P_V(j) + Theta_{V2,j} * P_V(j)^2]$$

Accuracy of the above mathematical models could be improved by use of derived parameters. For example, a maximum value maximum value and time difference between the two waveforms can be derived from the pressure waveforms. Using a derived parameter dataset rather than analysis over a large time series will reduce the "error" term in the cost calculation. Without parameter extraction of the raw data, many more samples will need to be processed to eliminate the error.

A more complex solution to the equation is through decomposition of the time signal into its Intrinsic Mode Functions or IMF. Intrinsic Mode Functions (IMF) can be used to improve accuracy at the expense of increased complexity/computation. Recent work has been done by Norden E. Huang in the form of the Hilbert-Huang Transform (HHT). This approach uses Empirical Mode Decomposition (EMD) and Hilbert Spectral Analysis (HAS) to improve accuracy, with drawback of increased computational expense. In a particular embodiment, the mathematical equation hypotheses discussed above are tested, and HHT techniques are implemented only if the mathematical hypotheses are unsatisfactory.

Drainage device 120 is capable of determining information in addition to volume of fluid in fluid canister 108 using, at least in part, pressure data from pressure sensors 126, 128. Additionally, certain embodiments further include one or more valve sensors (not shown) or programmed timing of the valve to detect the state of one or more valves in drainage device 120. In these embodiments, ECM 102 uses valve data from the valve sensors, along with data from pressure sensors 126, 128, for example, to determine additional information. ECM 102 determines this additional information, for example, using Linear Regression techniques, such as techniques similar to those discussed above for determining fluid canister 108 fluid volume. As another example, in some embodiments, ECM 102 determines additional information using Logistic Regression (also called Classification, probability output/Class present).

As discussed above, drainage device 120 is capable of estimating approximate volume of fluid in fluid canister 108. Accuracy of such an estimate is inversely proportional to the fluid volume due to changes in the system's "air capacity" in fluid canister 108. Additionally, certain embodiments are capable of detecting fine volume changes using information characterizing filter changes over time. Drainage device 120 determines filter changes, for example, by detecting change in resistance of a variable resistor, due to dampening of the filter. Furthermore, some embodiments are capable of detecting a heavily dumping patient 110, such as due to a broken stitch or suture, based on how fluid canister 108 volume may change over time.

Some embodiments are capable of determining air flow (also considered a fluid) through fluid canister 108 via a Liner Regression Model including, within drainage device 120, valve data from operation of a patient pressure relieving valve 130 and CDU pressure data from pressure sensor 128. Accuracy is increased, for example, by using feedback from the system and information characterizing change in current air passing. Moreover, some embodiments are capable of allowing for a tidal of air to enter fluid canister 108 and holding a valve to approximate the air pressure before release, to further promote accuracy. In these embodiments, drainage device 120 typically only holds the pressure for a split second to achieve better clinical data without significantly affecting therapy. Safety limits would be set around a feature such as this one. Pressure time decay data can be used to help approximate the volume/bolus passed to be summed over a time period to report air flow rate.

Respiration rate could be found using a similar approach but may require a large time data set (or samples from above data set).

Certain embodiments of drainage device 120 are capable of determining the existence, or probability of existence, of one or more of the following events using one or more Logistic Regression models:

Volume Data from Linear Regression is valid
   Pressure signals not similar enough to training examples
   Possible error in reported Volume
fluid canister 108 Filter Clogging, please replace CDU
Patient is breathing
Patient is inhaling
Patient is exhaling
   Calculated breaths/min based upon above events
Patient condition, such as Patient in repertory distress (e.g., coughing, choking, laughing, crying, etc.)
Tube Clogged (e.g., Fully occluded)
Degree of Tube Occlusion
Fluid in Line
Patient Dumping Fluid Certain embodiments of the systems and methods disclosed herein achieve one or more of the following advantages:

Better patient recovery time;
A tube line clearing device (TLC) can be embedded as part of drainage device 120 to clear the drainage tube when needed, and to detect dependent loops, monitor fluid collection and rate, air flow and rate;
TLC can be activated when there is a high degree of confidence there is a dependent loop and fluid collecting. This will extend battery life, with less disruption to therapy with un-needed TLC firing. There is less risk to patient when activating TLC with no clog.
Patient safety is improved through better monitoring, e.g., the system can detect if a patient is connected properly to system and/or if the patient is breathing. Clinical help can be summoned in this extreme case.
The system can determine if a drainage tube is occluded or has fluid blocking a path, fire TLC upon fluid blockage and alert clinical on kinked tube, and the like.
The system provides more value in the data to record in patient record or for use in research or to send to central nursing stations
Systems networked into Central Nursing Stations can provide the nursing staff with information for the following:
   Respiration Rate (Patient Tube Disconnected, Sleep or non-sleep related Apnea)
   Patient Distress
   Volume of Fluid
   Air Flow rate
   Tube patency
   Patient actively dumping fluid.

In certain embodiments, the methods, device and software of the present invention are implemented after capturing a training set of data and then a test set recorded from the ECM. The training set of data contains, for example, many samples at 10 ml volume increments. High variance (interpolated samples may have higher than expected error) in the calculations is addressed with additional training samples as well as modifications to the cost function and/or parameter set.

In various exemplary embodiments, the sample data set may contain "bad" data at different times/volumes. "Bad" data would be considered measurements where the system model has been violated and no longer acts with sufficient predictive certainty. One "bad" data example is data acquired when fluid is trapped in the drainage line or a clamp installed on the line. Additional "bad" examples might include sudden changes in respiration such as a cough and no respiration. Another example might include an air leak at different volumes.

One of skill in the art will recognize the availability of a variety of tools such as Matlab, and a free tool called Octave, to be used to analyze the data to find "theta" and then solve for volume and other parameters, as required.

Logistic Regression

In certain embodiments, logistic regression is applied to develop a system which generates a classification of the inputs (e.g., Yes/No for clogged status, data valid/data not valid, patient breathing, etc.). Logistic regression is very similar to the above Linear Regression, with the equation hypothesis wrapped by the Sigmoid Function whose output is from 0 to 1.

$$\text{sigmoid}(x) = \frac{1}{1+e^{-x}}$$

Expressed as a logistic hypothesis, the equation can take the form of:

$$\text{Logistic\_h}(T) = \text{sigmoid}(h(T)) = \frac{1}{1+e^{-h(T)}}$$

The cost function is changed to keep a convex solution to help avoid local minima. The new form of the cost function where y is a 1 if it belongs to the class and 0 if it does not:

$$J(\text{Theta}) = \frac{-1}{m}\sum_{i=1}^{m}[y^i * \log(h_{Theta}(x^i)) + (1-y^i)*\log(1 - h_{Theta}(x^i))]$$

The partial derivative is similar only in terms of the classifier y (0 or 1):

$$\frac{\partial}{\partial Theta_x}J(\text{Theta}) = \frac{1}{m}\sum_{i=1}^{m}[h_{Theta}(T)^i - y_{Theta}(T)^i]*X_x^i$$

Classifications are done, for example, in an One vs All structure. That is, for each classification, the neural network would be trained such that only the class being trained is "in the class" or 1. All other samples will be "out of the class" or otherwise set for 0. This means that there will be a different "theta" set for each classification desired.

Support Vector Machine Approach

Support vector machines are well suited and specialized in classification. By splitting all the above Logistic regression into a trained Support Vector Machine, (SVM) one gets a computationally efficient system generating a probability of a class being present in the input data.

SVMs differ from Logistic Regression in that a SVM "stores" the positive examples within its hyperplane (n-dimensional space). It then reports how close a sample is to one of the learned examples. The kernel selection is useful and defines the probability of the sample in relation to a known positive in the hyperplane. An open-source and optimized C++ library called "libSVM" may be used to prototype and/or be integrated into drainage device 120 for class prediction, according to a variety of example embodiments.

For the machine learning system to generalize to conditions that were not taught, the features themselves need to be general. For example, using the absolute pressure magnitude of both pressure sensors 126, 128 may not generalize well. The pressure applied to patient 110 and by the patient will be related to (i) the prescribed negative pressure and the force applied by the patient's respiratory system, and (ii) amount of air dead volume in the patient's pleural space.

The data received from pressure sensors 126, 128 is dependent upon the fluid canister 108 fluid volume, and features that are more generic can be formed. The following is a partial list of features that may be used in certain embodiments:

Peak Delay (e.g., time in units of microseconds or milliseconds)—Using the slowest pressure sensor waveform (most likely fluid canister 108 pressure), report the time from its peak pressure back to the peak pressure of the vent pressure peak.
Period Max-Min (pressure) for Vent
Distance between Vent Pressure peaks (in units of time such as milliseconds)
Period Max-Min (pressure) for fluid canister 108
Distance between fluid canister 108 Pressure peaks (in units of time such as milliseconds)
Pressure delta between fluid canister 108 & Vent at Vent Pressure Peak
Pressure delta between fluid canister 108 & Vent at CDU Pressure Peak
Slope of Vent pressure (leading to peak)
Slope of fluid canister 108 pressure (leading to peak)
Area under Pressure Curves
Valve Timing (Open/Closed times)

One embodiment of the present invention features Machine Learning through Genetic Programming (GP). Unlike the Genetic Algorithm and Machine Learning approaches which optimize an assumed solution, GP creates a "program" to solve the problem. The result of the learning process is a "formula/source code" which solves the applied problem.

There are several different approaches to Genetic Programming, including the following:
GP—Standard Genetic Programming based upon a functional tree of instructions
LGP—Linear Genetic Programming, fixed instruction length linearly processed (Fast)
CGP—Cartesian Genetic Programming, Fixed grid of random instruction points randomly wired
An example of a commercially available LGP application which can generate C code to easily embed within the software 104 is Discipulus 5 Genetic Programming Predictive Modeling (RML Technologies, Inc., Littleton, Colo., http://www.rmltech.com/).

In certain embodiments, the vent pressure sensor 126 may be omitted. This may occur for instance if characteristics of an externally applied stimulus are known. Volume and other features may still be determined using the CDU pressure sensor 128 in fluid canister 108 based upon the known patient source. For example, where a patient is on a heart-lung machine or ventilator, such external stimulus is known.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A method for determining at least one patient parameter including fluid volume measurements in a patient having a drain tube for draining fluid from a patient and having a first end and a second end, the first end fitted into the patient chest cavity and the second end in fluid communication with a collection vessel, at least one of the collection vessel and the drain tube having a first pressure sensor sensing the pressure within at least one of (i) the drain tube in a location proximal to the collection vessel, and (ii) the collection vessel, and a second pressure sensor sensing the pressure within the drain tube at a location distal to the collection vessel, wherein the at least one patient parameter further includes whether the drain tube is occluded or has fluid blocking a drainage path provided by the drain tube, the method comprising the steps of:

a. obtaining on a computer at least a first pressure value from the first pressure sensor and at least one second pressure value from the second pressure sensor and successive pressure values from the first pressure sensor and the second pressure sensor;
b. storing on the computer the pressure values as time series pressure data in computer memory;
c. reading the time series pressure data and extracting pressure features from the time series pressure data with the computer that determines whether the extracted pressure features are valid;
d. when the extracted pressure features are valid, then calculating with the computer the fluid volume measurements by processing the extracted pressure features through a non-linear solver using a non-linear equation, and when the extracted pressure features are not valid, then reading additional time series pressure data and extracting additional pressure features from the additional time series pressure data with the computer until the additional extracted pressure features are valid; and
e. activating a tube line clearance device in order to clear the drain tube in response to a determination by the computer that the drain tube is occluded or has fluid blocking the drainage path, or not activating the tube line clearance device in response to no determination by the computer that the drain tube is occluded or has fluid blocking the drainage path.

2. A device for determining at least one patient parameter in a patient, wherein the at least one patient parameter includes fluid volume measurements, wherein the device comprises:
a collection vessel;
a drain tube for draining fluid from the patient and having a first end and a second end, the first end configured to be fitted into and/or establish fluid communication with the patient's chest cavity, and the second end received in the collection vessel;
a first pressure sensor constructed and arranged to sense the pressure within at least one of (i) the drain tube in a location proximal to the collection vessel and (ii) the collection vessel;
a second pressure sensor constructed and arranged to sense the pressure within the drain tube at a location distal to the collection vessel;
wherein the first pressure sensor and the second pressure sensor are in signal communication with a computer means having memory, and wherein the at least one patient parameter further includes whether the drain tube is occluded or has fluid blocking a drainage path provided by the drain tube, and the computer means is configured to i. obtain a first pressure value from the first pressure sensor and a first pressure value from the second pressure sensor and successive pressure values from the first and second pressure sensors;
ii. store the pressure values as time series pressure data in the memory;
iii. read the time series pressure data and extract pressure features from the time series pressure data and determine whether the extracted pressure features are valid;
iv. when the extracted pressure features are valid, then calculate fluid volume measurements by processing the extracted pressure features through a non-linear solver using a non-linear equation, and when the extracted pressure features are not valid, then read additional time series pressure data and extract additional pressure features from the additional time series pressure data until the additional extracted pressure features are valid; and
v. activate a tube line clearance device in order to clear the drain tube in response to a determination by the computer means that the drain tube is occluded or has fluid blocking the drainage path, or not activate the tube line clearance device in response to no determination by the computer means that the drain tube is occluded or has fluid blocking the drainage path.

3. The device of claim 2, wherein the first pressure value from the first pressure sensor, the first pressure value from the second pressure sensor, and the successive pressure values from the first and second pressure sensors are obtained at timed intervals.

4. The device of claim 2, wherein the computer means comprises a user interface, and wherein the computer means produces an output displaying the at least one patient parameter on the user interface.

5. The device of claim 2, wherein said non-linear equation is implemented in one or more approaches selected from the group consisting of Support Vector Machine Approach, Artificial Neural Networks, Genetic Algorithms and Genetic Programming.

6. The device of claim 2, wherein said non-linear equation is expressed as:

$$h(T) = f(P_c(t), P_v(t)) = Theta_{bias} + \sum_{j=0}^{N} [Theta_{C1,j} * P_C(j) + Theta_{C2,j} * P_C(j)^2 + Theta_{V1,j} * P_V(j) + Theta_{V2,j} * P_V(j)^2]$$

wherein:
T=Represent current time (t=0), or point at fixed time after data
t=Integer time sample, 0 most current, N—oldest
f(x,y)=An unknown function dependent upon x & y
h(T)=Volume of fluid in fluid canister
$P_V(t)$=Pressure as a function of time at Vent,
$P_C(t)$=Pressure at CDU side of patient as a function of time,
N=Number of time samples required for calculation
Theta=Set of all Theta's listed below
$Theta_{bias}$=Arbitrary DC bias constant for hypothesis
$Theta_{c,t}$=Arbitrary parameter coefficient for CDU Pressure at time t
$Theta_{V,t}$=Arbitrary parameter coefficient for Vent Pressure at time t.

7. The device of claim 2, wherein said fluid is a biological fluid comprising any one of the group consisting of gas, water, serum, blood, plasma, lymph, pus therapeutic infusion fluids and mixtures thereof.

8. The device of claim 2, wherein said computer means monitors at least one additional patient parameter selected from the group consisting of error in volume data, error in flow data, filter clogging, breathing status, and excessive fluid movements.

9. The device of claim 2, wherein the patient parameter includes an estimation of liquid fluid collected in a collection vessel.

10. The device of claim 2, wherein said non-linear solver is trained.

* * * * *